US005722806A

United States Patent [19]

Erickson et al.

[11] Patent Number: 5,722,806
[45] Date of Patent: Mar. 3, 1998

[54] SYSTEM FOR COUPLING A TOOLHOLDER UTILIZING A FREE FLOATING WEDGING BALL

[75] Inventors: Robert A. Erickson, Raleigh; Anthony L. Barkley, Knightdale, both of N.C.

[73] Assignee: Kennametal Inc., Latrobe, Pa.

[21] Appl. No.: 556,115

[22] Filed: Nov. 9, 1995

Related U.S. Application Data

[63] Continuation-in-part of Ser. No. 168,802, Dec. 16, 1993, Pat. No. 5,466,102.

[51] Int. Cl.$^6$ ................................................. B23B 31/00
[52] U.S. Cl. ........................... 409/233; 82/160; 279/2.1; 279/2.24; 408/239 R; 403/322; 403/328
[58] Field of Search ..................... 408/238, 239 R, 408/240; 409/231, 232, 233, 234; 279/2.11, 2.12, 2.24, 2.1; 82/158, 160; 403/297, 321, 322, 328

[56] References Cited

U.S. PATENT DOCUMENTS

| 4,135,848 | 1/1979 | Hughes et al. | 409/233 |
|---|---|---|---|
| 4,709,454 | 12/1987 | Barnes | 24/590 |
| 4,844,671 | 7/1989 | Reinauer | 408/239 R |
| 4,932,295 | 6/1990 | Erickson | 82/160 |
| 4,978,262 | 12/1990 | Tjernström | 279/2.12 |
| 5,143,495 | 9/1992 | Bosek | 409/233 |
| 5,150,995 | 9/1992 | Reinauer | 409/234 |
| 5,346,344 | 9/1994 | Kress et al. | 279/2.12 |
| 5,443,340 | 8/1995 | Reinsauer et al. | 408/239 R |
| 5,466,102 | 11/1995 | Erickson | 409/232 |

FOREIGN PATENT DOCUMENTS

| 339321 | 11/1989 | European Pat. Off. | 279/2.24 |
|---|---|---|---|
| 4309237 | 9/1994 | Germany | 279/2.11 |

OTHER PUBLICATIONS

German Standard "Hollow Taper Shanks for Automatic Tool Exchange", Draft DIN 69 893 Part 1, Aug. 1991, Price Group 6, p. 1–4.

"The Future of Toolholding," 1992 GTE Valenite Corporation, 8 pages.

"The New Dimension," MAPAL Clamping Chuck KS, 4 pages.

Baker, Brian, "Tool–Spindle Connection System According to German DIN.69893 PT.2," 31 pages.

*Primary Examiner*—Daniel W. Howell
*Attorney, Agent, or Firm*—John J. Prizzi

[57] ABSTRACT

A coupling system is provided that includes a male coupling having a cylindrical distal end including a recess that includes follower surfaces, a female coupling having a cylindrical interior for receiving the distal end of the male coupling, and a pair of opposing jaw members movably mounted within the interior and including external cam surfaces for engaging the follower surfaces of the male coupling when the jaw members are radially moved apart, and a drive train for radially and forcefully moving the jaw members apart. The drive train includes a wedging ball that freely floats in recesses between the opposing jaw members, and a drive rod for axially moving the wedging ball into and out of engagement with wedge surfaces located in the interior of the jaw members. The drive rod includes a distal end having a bore for slidably receiving the wedging ball. The free-floating of the wedging ball within the drive rod bore and between the internal surfaces of the jaw members allows it to apply uniform wedging forces to the jaw members when spreading them apart into a coupling position.

33 Claims, 6 Drawing Sheets

FIG_10

SYSTEM FOR COUPLING A TOOLHOLDER UTILIZING A FREE FLOATING WEDGING BALL

This application is a continuation-in-part of United States patent application Ser. No. 08/168,802, filed Dec. 16, 1993 now U.S. Pat. No. 5,466,102.

BACKGROUND OF THE INVENTION

This invention generally relates to a system for coupling toolholders, and is specifically concerned with a system for detachably coupling toolholders of a modular tooling system to a toolholder, that utilizes a free floating wedging ball to generate a high holding force and to provide accurate and rigid tool couplings in all six degrees of freedom at both low and high speeds.

Coupling systems for interconnecting toolholders are well known in the prior art. Such coupling systems include a hollow, frustro-conical male component that forms part of the toolholder which mates with a frustro-conical opening in a female component. The female component is typically part of a spindle. The taper of both the frustro-conical components often has a slope of about 1 to 10 with respect to the axis of the toolholder. Such a slope provides a rigid, on-center interference coupling when the components are pulled together by a clamping mechanism disposed in the interior of the female opening.

There are presently a variety of mechanisms for clamping together frustro-conical male and female components. In some of these mechanisms, the female component on the spindle includes radially movable locking balls for engaging complementarily-shaped socket openings in the walls of the male component. When moved radially outwardly, the locking balls function to secure and pull in the frustro-conical toolholder shank into the frustro-conical opening in the spindle. An axially slidable bolt having cam surfaces radially forces the locking balls outwardly into the socket openings. In other types of mechanisms, the female opening includes a radially expandable locking plunger which is extendable into the hollow interior of the frustro-conical male component. The locking plunger may include two or more radially movable fingers that engage openings in the wall of the frustro-conically shaped male component in order to forcefully wedge the male component of the tool into the female component of the toolholder.

While both of these general types of prior art coupling systems have shown themselves to be effective for their intended purpose, systems fabricated by different manufacturers are not interchangeable with one another. Thus, the end user of a tooling system has, in the past, been forced to choose between one particular proprietary type of coupling system or another. To remedy this problem, the German government in 1987 standardized the dimensions of the envelope that such coupling systems were to have in a proclamation entitled "DIN 69890." However, this proclamation did not standardize the aspect ratio or type of coupling mechanism that was to clamp together the frustro-conical male and female coupling components. Specifications for a coupling system sufficiently standardized to permit interchangeability did not occur in Germany until the issuance of DIN 69893 in 1993, which sets forth the dimensions of the frustro-conical male component and female taper area that would secure the components together. This proclamation also specifies that the male component is to have an annular shoulder circumscribing its interior that defines a follower surface. By implication, the female component is to have a member with a cam surface that engages the male follower surface to lock the two components together. The standardized coupling system specified in DIN 69893 is already being manufactured by several companies. The growing implementation of DIN 69893 is likely to result in widespread adoption of these same specifications.

DIN 69893 generally sets forth the dimensions and type of follower surfaces in the male component that is to be used to couple the components together. However, it does not specify the form that any cam-bearing members in the female component should take, or what drive mechanism is to be used to move these cam-bearing members into engagement with the follower surface within the male component, as different cam-bearing members and drive mechanisms can be used without impairing the interchangeability of toolholders fabricated by different manufacturers.

There presently exists a number of such cam designs and drive mechanisms. Unfortunately, there are a number of shortcomings associated with each. For example, many prior art drive mechanisms employ a frustro-conical or ramp-shaped wedging element that radially expands the cam-bearing members. When such a wedging element is pulled between the cam-bearing members, they each pivot outwardly thereby engaging their exterior cam surfaces against the follower surfaces in the male component, thus locking the components together. Such an arrangement is capable of providing a firm coupling. However, the variable angle of engagement between the interior surfaces of the cam-bearing members and the conical or ramp-type surfaces of the wedging element that is caused by the pivoting action results in only line-type contact between the wedging element and the interior surfaces of the cam-bearing members. Such line contact not only hastens the wear of these components by the unwanted concentration of stresses, but further interferes with the smoothness of operation. Additionally, because the frustro-conical or ramp-type wedging element is rigidly affixed to the draw bar, any asymmetries in the interior surfaces of the jaw members can cause non-uniformities in the wedging forces applied between these members. This, in turn, can jeopardize the rigidity of the resulting joint (as one of the cam-bearing members may be completely engaged to the male member while the other is not). Finally, such an arrangement makes it difficult to adjust the mechanical advantage between the wedging member and the cam-bearing members. If the system operator wishes to change the mechanical advantage between these components, it is necessary not only to change the jaw members, but also the wedging member, and probably the draw bar as well, since the wedging members and draw bars are often integrally formed.

While some of the aforementioned deficiencies of conical or ramp-type wedging members could be overcome by the use of the previously described locking ball mechanism, the use of locking balls requires the provision of holes through the tapered wall of the male component of the tool. Such holes are not allowed in the specification of DIN 69893.

Clearly, there is a need for a drive mechanism for radially expanding the cam-bearing members needed in DIN 69893 coupling systems which avoids line contact between the wedging member and the interior surfaces of the cam-bearing members which could result in excessive wear, shortened tool life, and smoothness of operation. Ideally, the wedging member used in the drive mechanism would apply the same amount of spreading forces to both of the cam-bearing members despite asymmetries or inaccuracies in the portion of their interior surfaces that come into contact with the wedging member so that the rigidity of the resulting coupling is never compromised by such asymmetries or inaccuracies. It would be desirable if the mechanical advantage between the axial movement of the wedging element and the radial movement of the cam-bearing members could be easily adjusted by the replacement of only a very few parts in the system. Finally, the system should be relatively easy and inexpensive to manufacture, and easy to assemble and disassemble, and maintain.

SUMMARY OF THE INVENTION

Generally speaking, the invention is a coupling system that fulfills all of the aforementioned criteria while eliminating or at least ameliorating the shortcomings associated with the prior art. The coupling system of the invention comprises a male coupling having a recess that includes follower surfaces, a female coupling having a hollow interior for receiving the male coupling, a pair of opposing jaw members movably mounted in the hollow interior having cam surfaces on their exteriors for engaging the follower surfaces in the interior of the male coupling when the jaw members are moved apart, and a drive train for forcefully moving the jaw members apart. The drive train includes a rounded wedging element which may be a wedging ball that freely floats between the opposing jaw members, a drive rod for axially moving the wedging ball into and out of engagement with wedge surfaces located in the interior of the jaw members, and a compliant connection between the wedging ball and the drive rod so that the wedging ball floatingly engages the internal wedge surfaces of both of the opposing jaw members with equal force.

The compliant connection may take the form of a cylindrical bore that completely extends through a distal end of the drive rod and which slidably receives the wedging ball. Additionally, the internal wedge surfaces of the opposing jaw members may each have a semi-cylindrical profile whose curvature is substantially the same as the curvature of the wedging ball such that lenticular (as opposed to line) contact is made between these surfaces and the ball when the jaw members are spread apart. The angle of engagement between the wedging ball and the wedge surfaces is such that a mechanical advantage is created between the axial distance that the wedging ball is displaced by the drive rod and the distance that the jaw members are spread orthogonally with respect to the axis. In the preferred embodiment, the angle of engagement is selected so that the mechanical advantage is at least 3 to 1 at all points along the axial stroke of the drive rod. The axial contour of the semi-cylindrical wedge surfaces may be slightly curved so that the mechanical advantage remains substantially the same at all points along the axial stroke of the drive rod. The axial contour of the semi-cylindrical wedge may also be correlated to variations in the spring force over the spring stroke to obtain a substantially constant mechanical advantage.

The opposing jaw members are pivotally mounted on one end in the interior of the female coupling, and the wedging ball engages the interior of the jaw members at a point on an opposite end of each which is further away from the pivotally mounted ends than the cam surfaces located on the outside of the jaw members to provide still another mechanical advantage between the action of the wedging ball and the inter-engagement between the cam and follower surfaces of the jaw members and the male coupling, respectively.

The coupling system of the invention may further include both a jaw closing mechanism for bringing the jaw members together when the drive rod pushes the wedging ball away from the wedge surfaces of the jaw members, as well as a free floating fulcrum which is pivotally engaged by the proximal ends of the jaw members. The jaw closing mechanism may include wedging cam surfaces on the drive rod which engage inclined follower surfaces present on the back ends of each of the jaw members when the drive rod pushes the wedging ball out of engagement with the wedging surfaces of the jaw members. The free floating fulcrum is preferably formed from a fulcrum sphere that freely floats within a through-bore in the drive rod. The jaw closing mechanism advantageously secures the wedging ball when the coupling system is in a decoupled state, and provides a positive assurance that the wedging ball will not fall out of the system. The free floating fulcrum, in an action similar to the free floating wedging ball, advantageously equilibrates the forces experienced by the back ends of the jaw members as the result of the pivoting action of these members within the female coupling.

Finally, the stroke of the drive rod is such that the distal end is axially movable into contact with the male coupling in order to "bump" the male coupling out of engagement with the female coupling to disconnect the male and female couplings.

DETAILED DESCRIPTION OF THE PREFERRED EMBODIMENT

Figure 1:
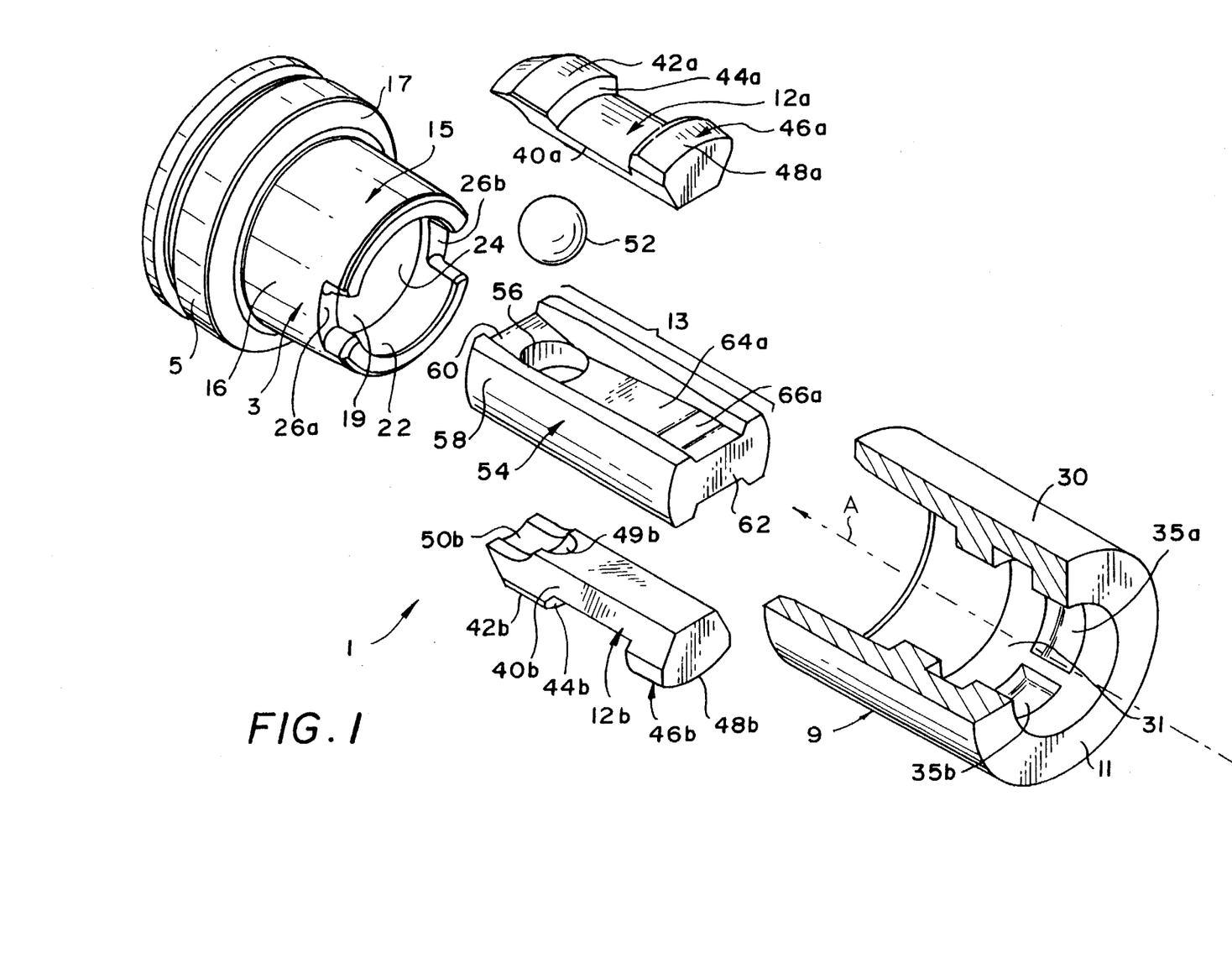
FIG. 1 is an exploded perspective view of the coupling system of the invention.

With reference to FIG. 1 wherein like numbers designate like components throughout all of the figures, the coupling system 1 of the invention comprises a male coupling 3 which is part of a toolholder 5 which may, for example, hold an insert (not shown) of the type used to cut metal. The system 1 further includes a female coupling 9 which is part of a base 11 which may be, for example, a spindle for turning the toolholder 5 and the associated male coupling 3. In operation, both the male and female couplings 3,9 may rotate around the axis A. However, this design is not limited to rotating applications and may be used in static applications, as well. As will be described in more detail later, the female coupling 9 is substantially hollow, and houses a pair of opposing jaw members 12a,b. These jaw members 12a,b are radially expandable by means of a drive train 13, and forcefully mate and interlock the male and female couplings 3,9 of the system 1.

Figure 2:
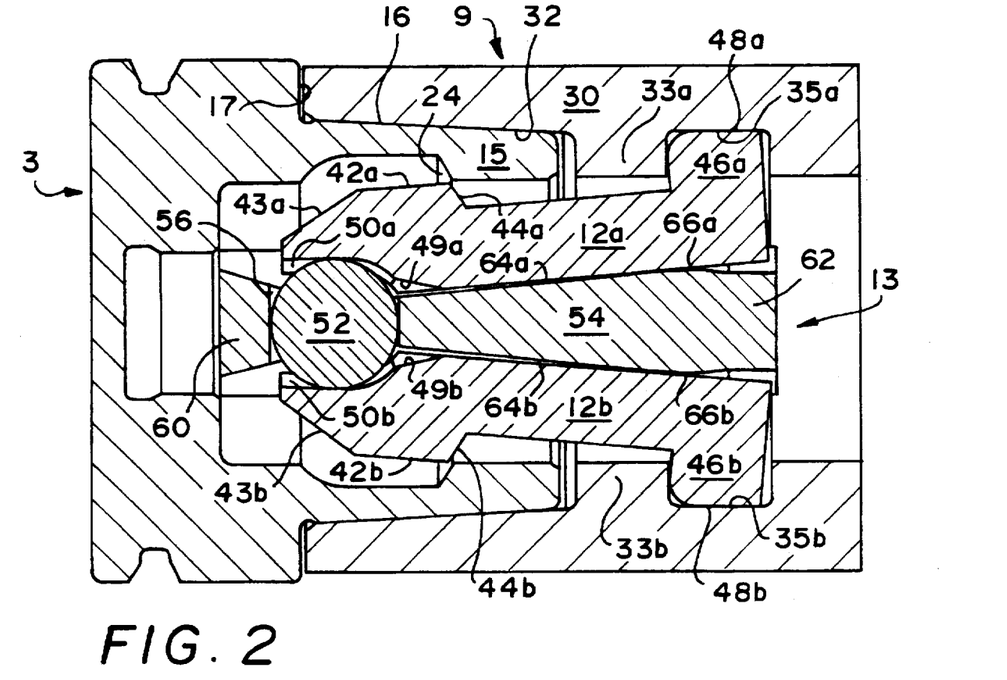
FIG. 2 is a cross-sectional side view of the coupling system of FIG. 1 as it would appear in assembled form with the wedging ball in an undriven state between the jaw members in order to facilitate the mating of the male and female couplings of the system.

As shown in FIGS. 1 and 2, the male coupling 3 includes a hollow shank 15 having a frustro-conical outer surface 16 which is preferably tapered at a slope of approximately 1 to 10 with respect to the axis of the male and female couplings 3 and 9. The proximal end of the frustro-conical shank 15 is an integral port of the toolholder 5. An annular coupling face 17 circumscribes the junction between the shank 15 and the toolholder 5. The shank 15 is skirt-shaped, and encloses a frustro-conical interior 19. The distal inner end of the shank 15 is circumscribed by an annular shoulder 22 that defines, on its rear face, a frustro-conical follower surface 24. As is best seen in FIG. 1, the distal end of the shank 15 also includes a pair of opposing alignment slots 26a,b for properly aligning the male coupling 3 within the interior of the female coupling 9 incident to the coupling operation.

With reference to FIGS. 1 and 2, the female coupling 9 has a generally cylindrical body 30 with a hollow interior 31 defined by a frustro-conical inner wall 32 that is complementary in shape to the outer surface 16 of the shank 15 of the male member 3. A pair of opposing, arcuate lugs 33a,b partially circumscribes the inner wall 32 of the cylindrical body 30 near its proximal end. These arcuate lugs 33a,b define a pair of opposing recesses 35a,b at the proximal end of the interior 31. Alternately, grooves may be used in lieu of the recesses 35a,b.

Figure 3:
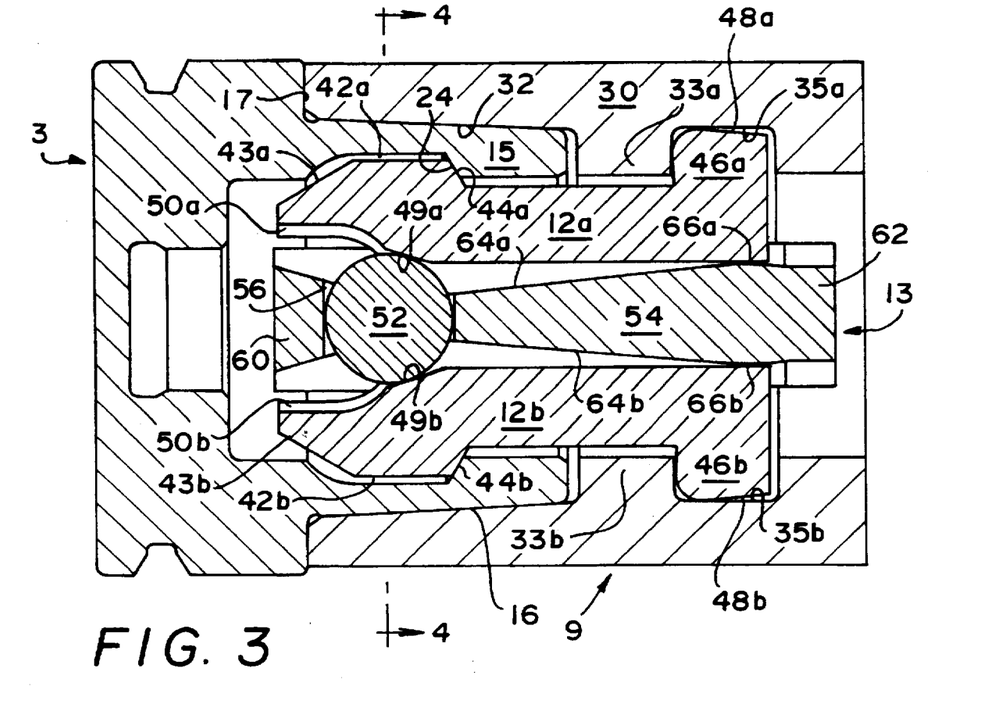
FIG. 3 is likewise a cross-sectional side view of the coupling system illustrated in FIG. 1 shown in assembled form, wherein the drive train has driven the wedging ball into tight engagement with the inner surfaces of the jaw members in order to forcefully secure the mated male and female couplings together.

With reference now to FIGS. 1, 2, and 3, the jaw members 12a,b each include an elongated body portion 40a,b. The distal end of each body portion 40a,b includes an arcuate ledge 42a,b. Each of these ledges includes a tapered lead-in surface 43a,b for facilitating the insertion of the jaws in the non-expanded state illustrated in FIG. 2 into the hollow interior 19 of the male coupling 3. Each of these ledges 42a,b further includes a cam surface 44a,b which is complementary in shape to the frustro-conical follower surface 24 of the annular shoulder 22 that circumscribes the interior of the male coupling 3. The proximal end of each of the elongated body portions 40a,b of the jaw members 12a,b includes a foot 46a,b having a tapered side 48a,b. The foot 46a,b of each of the jaw members 12a,b is insertable into the recesses 35a,b and pivotally movable on the proximal surface of each of the arcuate lugs 33a,b. The tapered sides 48a,b of each foot 46a,b allows the feet to pivot without interference with the inner surface of the female coupling 9. A rounded recess 50a,b is provided on the inner surface of the distal end each of the body portions 40a,b of the jaw members 12a,b.

With reference again to FIGS. 1, 2, and 3, the drive train 13 of the coupling system 1 generally comprises a wedging ball 52, and a drive rod 54 for engaging the outer surface of the ball 52 against the wedge surfaces 49a,b of the jaw members 12a,b. The wedging ball 52 is carried within a ball receiving opening 56 near the distal end 58 of the drive rod 54. It is important to note that the wedging ball 52 slidably "floats" in the ball receiving opening 56 of the rod 54 as it is being pulled into or pushed out of engagement with the wedge surfaces 49a,b. The free floating nature of the wedging ball 52 within the opening 56 allows it to apply an equal amount of wedging force to the jaw members 12a,b by moving slightly either way in the vertical direction (as seen in FIGS. 1 and 3) during a coupling or uncoupling operation. In this way, the wedging ball 52 can equally distribute the wedging force applied to the jaw members 12a,b despite variations in the angles or shapes of the wedge surfaces 49a,b of the jaw members 12a,b. One embodiment for the wedging ball 52 is a sphere made from bearing steel and having a hardness of between 58 to 60 Rockwell C.

The distal end 58 of the drive rod 54 further includes a bump member 60 for decoupling the male and female couplings 3,9 when the drive rod 54 is extended even further to the left than is shown in FIG. 2. The proximal end 62 of the drive rod 54 is connected to an extending and retracting means (not shown) which may, among other devices, be a stack of Bellville washers, a coil spring, or a hydraulic cylinder capable of forcefully extending or withdrawing the rod 54. Disposed between the distal and proximal ends 58,62 of the rod 54 are tapered recesses 64a,b. These recesses provide clearance in the drive rod 54 so that the jaw members 12a,b may assume the position illustrated in FIG. 2, which in turn allows them to be extended into or withdrawn from the hollow interior 19 of the male coupling 3 without interference. These tapered recesses 64a,b terminate on one side at the ball receiving opening 56, and at their other side at raised fulcrum portions 66a,b which provide pivot points for the feet 46a,b of the jaw members 12a,b.

Figure 4:
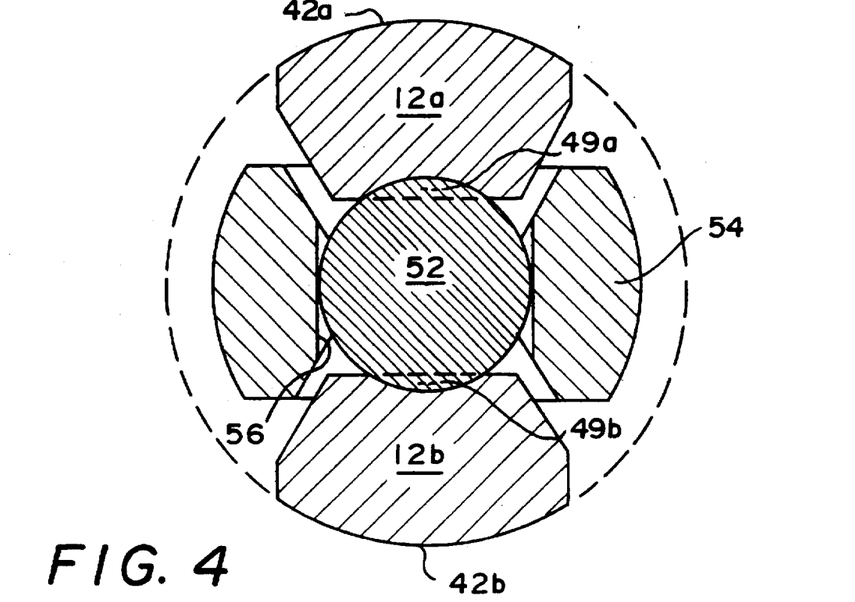
FIG. 4 is a cross-sectional front view of the coupling illustrated in FIG. 3 along the line 4—4.
Figure 5:
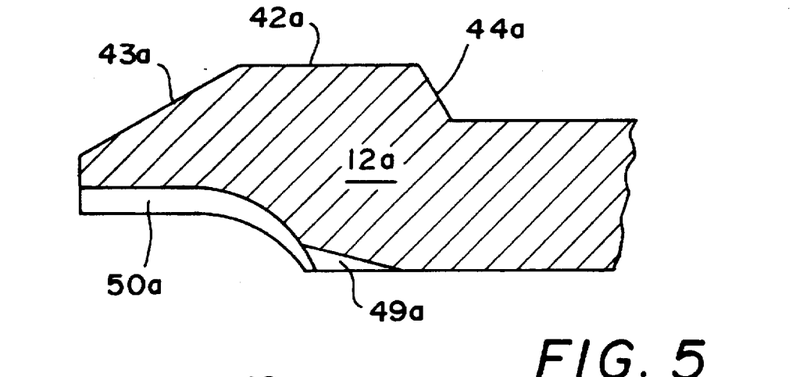
FIG. 5 is an enlarged, partial cross-sectional side view of only the upper jaw of the coupling, illustrating the linear wedging surface used in the first preferred embodiment of the invention.

FIGS. 4 and 5 illustrate the wedge surfaces 49a,b of the jaw members 12a,b used in the first preferred embodiment of the invention. From FIG. 4, it is evident that the wedge surfaces 49a,b have an arcuate or partial cylindrical profile that closely conforms to the sphericity of the wedging ball 52. Such dimensioning advantageously allows for a lenticular (as opposed to a point or line) contact between the wedging ball 52 and the wedge surfaces 49a,b. Note the linear profile of the wedge surface 49 with respect to the horizontally oriented underside of the jaw member 12a in FIG. 5. This surface, in conjunction with the pivoting motion caused by the feet 46a,b, causes non-linear movement between the axial displacement of the drive rod 54 and the radial displacement of the jaw members 12a,b. As the wedging ball 52 is drawn closer to the feet 46a,b of the jaw members 12a,b, the pivoting movement of the jaw members 12a,b causes the ball 52 to engage the wedge surfaces 49a,b at progressively steeper angles. Such steeper engagement angles create a loss in mechanical advantage as the wedging ball 52 is drawn toward the feet 46a,b of the jaw member 12a,b to spread them apart. Hence, a higher axial force (on the order of perhaps 20% greater) needs to be applied by the spring pack or hydraulic cylinder (not shown) that axially pulls the drive rod 54 into a locking position.

Figure 6:
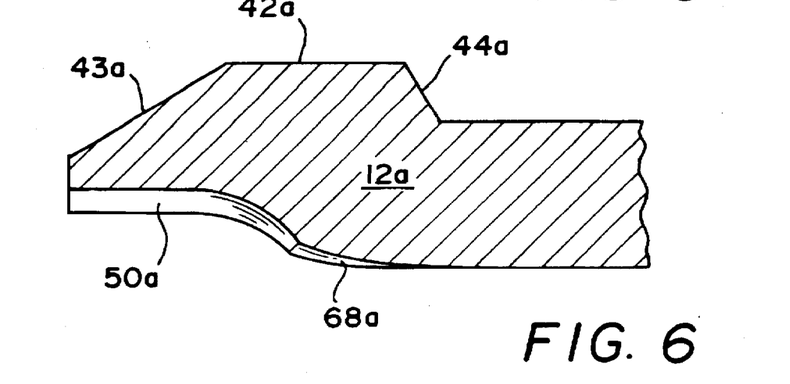
FIG. 6 is an enlarged partial cross-sectional side view of the upper jaw member of the coupling system, illustrating a curved wedging surface used in a second embodiment of the invention which allows the locking jaws to expand radially outwardly a distance which remains in linear proportion with respect to the distance the lock rod is drawn throughout the entire stroke of the lock rod.

To compensate for this decreased mechanical advantage, the contour of the wedge surfaces may be changed from a substantially cylindrical profile to a parabolic profile, as illustrated by the wedge surface 68a in FIG. 6. Such profiling results in a substantially linear relationship between the axial distance that the drive rod 54 is withdrawn by the spring package or hydraulic cylinder, and the extent to which wedge surfaces 49a,b of the jaw members 12a,b are pivotally moved in a radial direction. Because of this compensation, the mechanical advantage between the wedging ball 52 and the wedging surfaces 68a,b (of which only 68a is shown) is substantially constant throughout the entire stroke of the drive rod 54.

Figure 7:
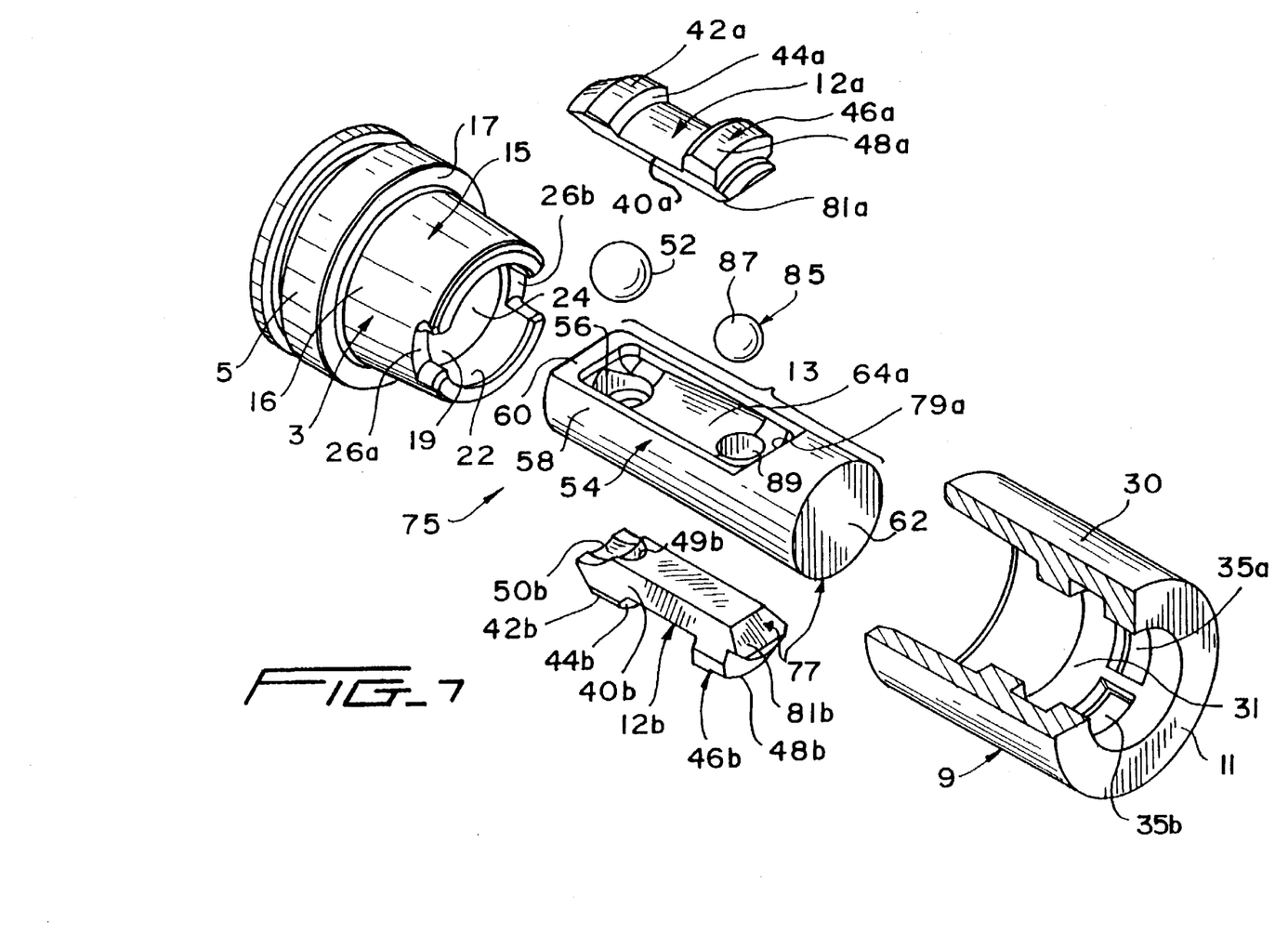
FIG. 7 is an exploded perspective view of an alternative embodiment of the coupling system of the invention.
Figure 8:
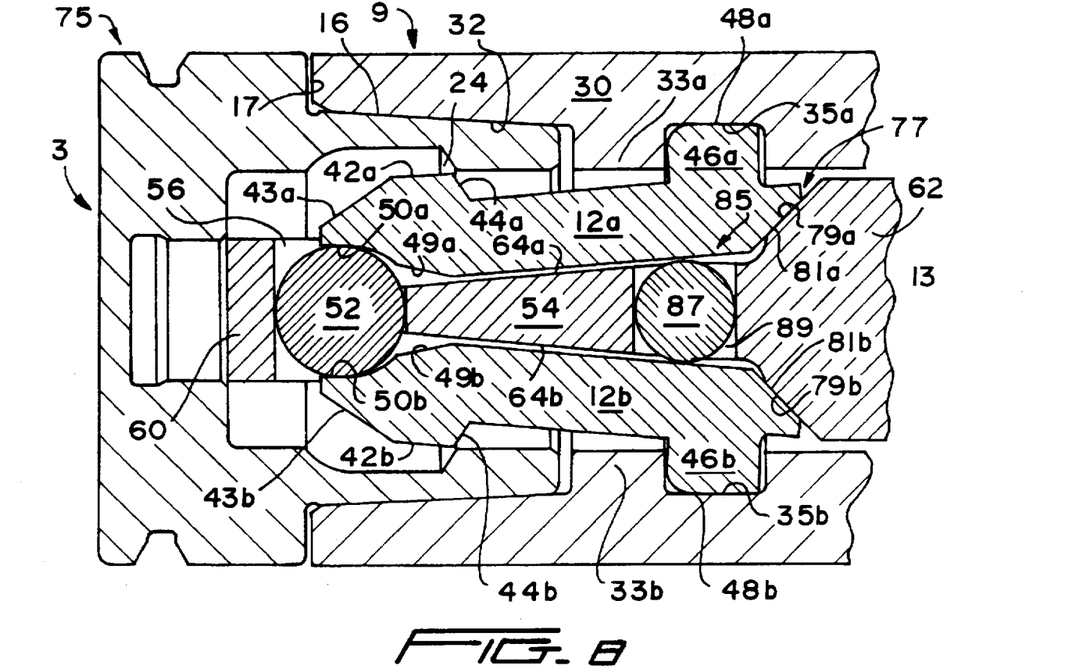
FIG. 8 is a cross-sectional side view of the coupling system of FIG. 7 as it would appear in assembled form with the wedging ball in an undriven state between the jaw members to facilitate the mating of the male and female couplings of the system.
Figure 9:
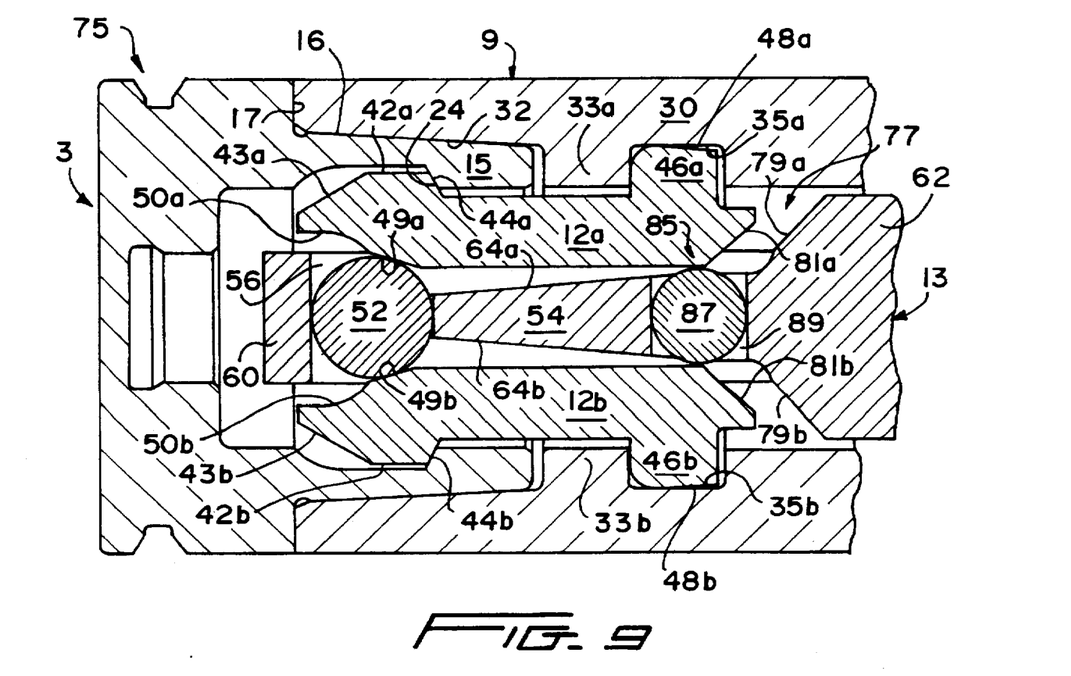
FIG. 9 is likewise a cross section side view of the coupling system illustrated in FIG. 7 shown in assembled form, wherein the drive train has driven the wedging ball into tight engagement with the inner surfaces of the jaw members in order to forcefully secure the mated male and female couplings together.

FIGS. 7, 8, and 9 illustrate an alternative embodiment of the coupling system 75 which includes, in addition to the previously described components, a jaw closing mechanism 77, and a free floating fulcrum 85.

Figure 10:
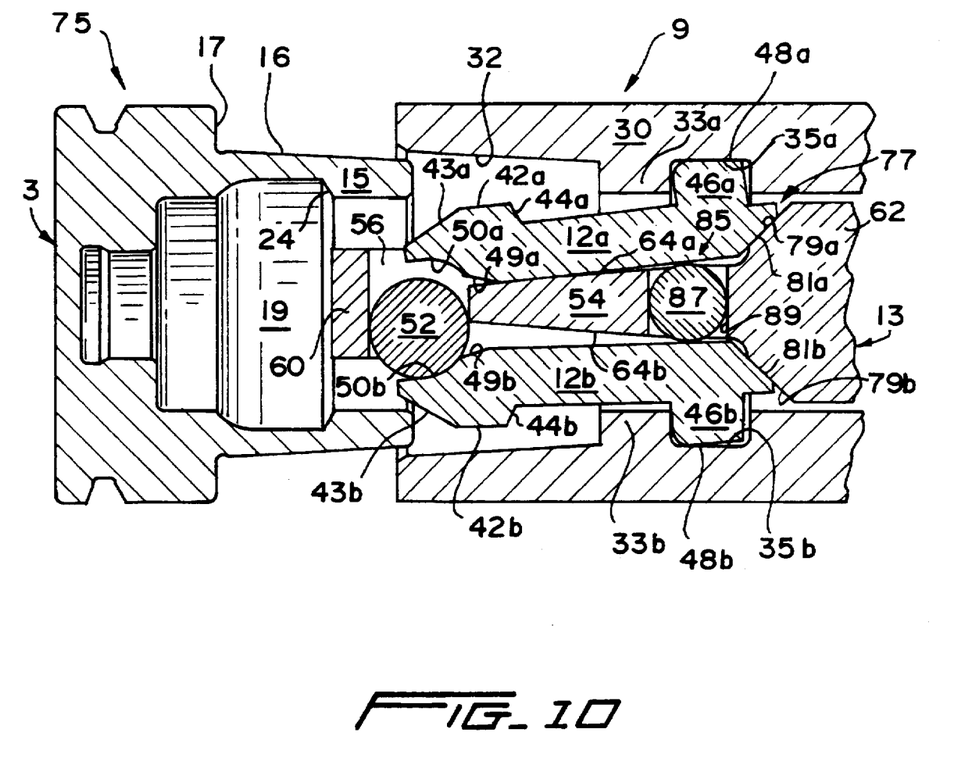
FIG. 10 is a cross-sectional side view of the coupling system illustrated in FIG. 7, illustrating the maximum extent that the jaw closing mechanism allows the jaw members to spread apart when the system is in a decoupled state.

With particular reference to FIGS. 8 and 9, the jaw closing mechanism 77 is formed from a pair of opposing, wedging cam surfaces 79a,b on the proximal end 62 of the drive rod 54, in combination with inclined follower surfaces 81a,b on the back ends of the jaw members 12a,b. When the drive rod 54 is pushed toward the male coupling 3 in the position illustrated in FIG. 8, these wedging cam surfaces 79a,b and inclined follower surfaces 81a,b engage one another as shown, thereby pivoting the front ends of the jaw members 12a,b together toward the wedging ball 52 as shown. Even when the male coupling 3 is removed from the female coupling 9 as shown in FIG. 10, the inner engagement between the cam and follower surfaces 79a,b and 81a,b does not allow the front end of the bottom jaw member 12b to drop below a point that would allow the wedging ball 52 to fall out. Hence, at all times, the wedging ball 52 is securely captured between the rounded recesses 50a,b of the jaw members 12a,b and the ball receiving opening 56 at the distal end of the drive rod 54. The inner engagement between the cam and follower surfaces 79a,b and 81a,b also allows the male coupling 3 and female coupling 9 to easily be engaged with the use of only short lead-in tapered surfaces 43a,b on the jaw members 12a,b.

The free floating fulcrum 85 is similar in structure to the previously described, freely floating wedging ball 52, and includes a fulcrum sphere 87 slidingly and floatingly captured in a through-bore 89 located at the proximal end 62 of the drive rod 54. The smooth, hard surface of the fulcrum sphere 87 provides a precision fulcrum pivoting point for each of the opposing jaw members 12a,b which simplifies the machining of the drive rod 54. Additionally, the free floating nature of the fulcrum sphere 87 evenly distributes the forces applied to the back ends of the jaw members 12a,b as a result of such pivoting.

The operation of the coupling system 1 is best understood with respect to FIGS. 2 and 3. As is illustrated in FIG. 2, in order to initially couple the male and female couplings 3,9, the drive rod 54 is moved toward the male coupling 3 such that the wedging ball 52 is captured on its upper and lower surfaces by the rounded recesses 50a,b at the distal ends of the jaw members 12a,b. When the wedging ball 52 is in such a position, the jaw members 12a,b can swing inwardly toward the drive rod 54 such that the tapered lead-ins 43a,b may be extended into the hollow interior 19 of the male coupling. In such a position, the cam surfaces 44a,b of the jaw members 12a,b are disposed radially inwardly with respect to the follower surface 24 of the male coupling 3. When the drive rod 54 is withdrawn by, for example, a spring pack or hydraulic cylinder into the position illustrated in FIG. 3, the wedging ball 52 engages the wedge surfaces 49a,b of the jaw members 12a,b as previously described, thereby radially extending the cam surfaces 44a,b into the follower surfaces 24 of the male coupling 3. Such a radial expansion of the jaw members 54a,b simultaneously creates an interference type joint between the male and female couplings 3,9 while pulling the male coupling 3 ever more tightly with the female coupling 9. To disconnect the male and female coupling 3,9, the drive rod 54 is again extended toward the male coupling 3 not only far enough to allow the jaw members 12a,b to pivot back into the position illustrated in FIG. 2, but further to "bump" the bump member 60 against the floor (not shown) of the male coupling 3, thereby ejecting the male coupling 3 from the female coupling 9. The operation of the alternative embodiment 75 of the coupling system is essentially the same as the coupling system 1. The only differences involve the operation of the previously described jaw closing mechanism 77 in moving the front ends of the jaw members 12a,b together when the drive rod 54 moves the wedging ball 52 towards the male coupling 3, and the operation of the free floating fulcrum 85.

While the coupling system of the invention has been described with respect to a preferred embodiment, various modifications, variations, and additions will become evident to persons of ordinary skill in the art. All such variations, modifications, and additions are intended to fall within the scope of this invention, which is limited only by the claims appended hereto.

What is claimed is:

1. A coupling system comprising:
   (a) a male coupling having a recess at a distal end that includes follower surfaces;
   (b) a female coupling having an axis, and a hollow interior disposed along said axis for receiving the distal end of said male coupling, and a plurality of opposing jaw members movably mounted in said interior and having external cam surfaces for engaging said follower surfaces when said jaw members are moved apart orthogonally with respect to said axis to mate said male and female couplings together, and internal wedge surfaces for engaging a wedging element, and
   (c) a drive train for moving said jaw members apart, including said wedging element, a drive rod axially movable between said opposing jaw members for driving said wedging element into and out of engagement with said internal wedge surfaces of said opposing jaw members, and means for compliantly connecting said wedging element to said axial driving means, said means for compliantly connecting being comprised of an opening in said drive rod that circumscribes said wedging element.

2. A coupling system as defined in claim 1, wherein said wedging element is free floating within said opening in said rod and opposing recesses in said jaw members.

3. A coupling system as defined in claim 2, wherein said wedging element is a wedging ball, and said opening is a bore through said drive rod that slidably receives said wedging ball.

4. A coupling system as defined in claim 3, wherein the wedging ball is made from bearing steel having a hardness of between 58 to 60 Rockwell C.

5. A coupling system as defined in claim 3, wherein the internal wedge surfaces of each of said opposing jaw members have a cylindrical profile whose curvature is substantially the same as said ball such that lenticular contact is made between said wedging ball and said internal wedge surfaces.

6. A coupling system as defined in claim 1, wherein said drive rod has a distal end axially movable into contact with said male coupling to bump said male coupling out of engagement with said female coupling.

7. A coupling system as defined in claim 1, wherein the opposing jaw members are pivotally mounted on one end in the hollow interior of the female coupling, and the wedging element engages the jaw members at a point on an opposite end of each jaw member which is further away from said one end of each jaw member than said cam surfaces to provide a mechanical advantage between the action of the wedging element driving apart the jaw members and the interengagement between the cam and follower surfaces of the jaw members and the male coupling, respectively.

8. A coupling system as defined in claim 1, wherein said drive train further includes means for moving said jaw members together when said axial driving means drives said wedging element out of engagement with said internal wedge surfaces of said opposing jaw members.

9. A coupling system as defined in claim 1, wherein said drive train further includes means for moving said jaw members together when said axially movable rod drives said wedging element out of engagement with said internal wedge surfaces of said opposing jaw members.

10. A coupling system as defined in claim 9, wherein said means for moving said jaw members together includes mutually inter-engaging cam and follower surfaces between said axially movable rod and said jaw members.

11. A coupling system as defined in claim 10, wherein said cam surfaces include opposing wedge surfaces on a portion of said axially movable rod, and said follower surfaces includes second internal wedge surfaces on each of said jaw members.

12. A coupling system as defined in claim 1, wherein said means for axially driving said wedging element includes a fulcrum, and said pair of opposing jaw members is pivotally mounted within said female coupling in engagement with said fulcrum.

13. A coupling system as defined in claim 12, wherein said fulcrum includes a fulcrum element compliantly mounted in said means for axially driving said wedging element in pivotal engagement with each of said opposing jaw members.

14. A coupling system as defined in claim 13, wherein said fulcrum element is a fulcrum sphere freely and floatingly movable in a through-bore in said means for axially driving said wedging element.

15. A coupling system tool component comprising:
(a) a male coupling having a cylindrical distal end including a recess that includes follower surfaces;
(b) a female coupling having a hollow interior for receiving the distal end of the male coupling, and a pair of opposing jaw members movably mounted within said interior and including external cam surfaces for engaging said follower surfaces when said jaw members are radially moved apart to mate said male and female couplings, and internal wedge surfaces for engaging a wedging ball, and
(c) a drive train for radially moving said jaw members apart, including said wedging ball, an axially movable rod for driving said wedging ball into and out of engagement with said internal wedge surfaces of said opposing jaw members, and means for compliantly connecting said wedging ball to said drive rod so that said ball floatingly engages the wedge surfaces of said opposing jaw members with equal force.

16. A coupling system as defined in claim 15, wherein said compliant connection means is an opening in said drive rod that slidably receives said wedging ball.

17. A coupling system as defined in claim 16, wherein said wedging ball is free floating within a space defined by said drive rod opening and internal recesses within said opposing jaw members.

18. A coupling system as defined in claim 17, wherein the internal wedge surfaces of each of said opposing jaw members have a cylindrical profile whose curvature is substantially the same as said ball such that lenticular contact is made between said wedging ball and said internal wedge surfaces.

19. A coupling system as defined in claim 17, wherein the wedging ball is made from bearing steel having a hardness of between 58 to 60 Rockwell C.

20. A coupling system as defined in claim 15, wherein said drive rod has a distal end axially movable into contact with said male coupling to bump said male coupling out of engagement with said female coupling.

21. A coupling system as defined in claim 15, wherein the opposing jaw members are pivotally mounted on one end to the female coupling, and the wedging ball engages the jaw members at a point on an opposite end of each jaw member which is further away from said one end of each jaw member than said cam surfaces to provide a mechanical advantage between the action of the wedging ball driving apart the jaw members and the inter-engagement between the cam and follower surfaces of the jaw members and male coupling, respectively.

22. A coupling system as defined in claim 15, wherein the angle of engagement between said wedging ball and said wedge surfaces of said opposing jaw members is such that a mechanical advantage is created between the axial distance that the wedging ball is displaced and a distance that said jaw members are displaced orthogonally with respect to said axis.

23. A coupling system as defined in claim 22, wherein said mechanical advantage is at least 3 to 1 at all points along said axial movement of said drive rod.

24. A coupling system as defined in claim 22, wherein said internal wedge surfaces of said jaw members are contoured to maintain said mechanical advantage at substantially the same value at all points along said axial movement of said drive rod.

25. A coupling system as defined in claim 15, wherein said drive train further includes means for moving said jaw members together when said axially movable rod drives said wedging ball out of engagement with said internal wedge surfaces of said opposing jaw members.

26. A coupling system as defined in claim 25, wherein said means for moving said jaw members together includes mutually inter-engaging cam and follower surfaces between said axially movable rod and said jaw members.

27. A coupling system as defined in claim 15, wherein said axially movable rod includes a fulcrum element compliantly mounted therein in pivotal engagement with each of said opposing jaw members.

28. A coupling system as defined in claim 27, wherein said fulcrum element is a fulcrum sphere freely and floatingly movable in a through-bore in said axially movable rod.

29. A coupling system for lockably coupling together machine tool components, comprising:
(a) a male coupling having a cylindrical distal end including a recess that includes follower surfaces;
(b) a female coupling having a cylindrical interior for receiving the distal end of the male coupling, and a pair of opposing jaw members having one end pivotally mounted within said interior and opposite ends including external cam surfaces for engaging said follower surfaces when said jaw members are pivotally moved apart in order to mate said male and female couplings, and internal wedge surfaces for engaging a wedging ball, and (c) a drive train for pivotally moving said jaw members apart, including said wedging ball disposed between said jaw members for wedgingly spreading said jaw members apart when moved along the axis of rotation of said cylindrical interior of said female coupling toward opposite ends of said jaw members, a drive rod for axially moving said wedging ball into and out of engagement with said internal wedge surfaces of said jaw members, and a compliant connection between the wedging ball and the drive rod including a bore in said rod that slidably receives said ball so that said wedge surfaces of both of said jaw members are engaged with equal force, wherein the movement of each of said jaw members orthogonal to said axis is less than the axial movement of said wedging ball to provide a mechanical advantage between said wedging ball, and said jaw members.

30. A coupling system as defined in claim 29, wherein the ball engages the jaw members at a point on an end opposite from said pivotally mounted ends which is further away from said pivotally mounted ends than said cam surfaces to provide a mechanical advantage between the action of the wedging ball driving apart the jaw members and the inter-engagement between the cam and follower surfaces of the jaw members and male coupling, respectively.

31. A coupling system as defined in claim 30, wherein said wedge surfaces substantially complementary in curvature to the spherical outer surface of said wedging ball to provide lenticular type surface contact between said ball and said jaw members due to elastic deformation.

32. A coupling system as defined in claim 29, wherein said drive train further includes means for pivotally moving said jaw members together when said axially movable rod drives said wedging ball out of engagement with said internal wedge surfaces of said opposing jaw members, including mutually interengaging cam and follower surfaces between said axially movable rod and said jaw members.

33. A coupling system as defined in claim 29, wherein said axially movable rod includes a fulcrum sphere freely and floatingly mounted in a through-bore therein, and wherein each of said opposing jaw members is in pivotal engagement with said sphere.

* * * * *